United States Patent [19]

Liu et al.

[11] Patent Number: 5,866,165
[45] Date of Patent: Feb. 2, 1999

[54] COLLAGEN-POLYSACCHARIDE MATRIX FOR BONE AND CARTILAGE REPAIR

[75] Inventors: LinShu Liu, Sunnyvale; Robert C. Spiro, Half Moon Bay, both of Calif.

[73] Assignee: Orquest, Inc., Mountain View, Calif.

[21] Appl. No.: 783,650

[22] Filed: Jan. 15, 1997

[51] Int. Cl.$^6$ .............................. A61K 38/39; A61K 9/10; A61K 47/42; A61K 47/36
[52] U.S. Cl. ...................... 424/486; 424/78.3; 525/54.1; 525/54.2; 527/205; 530/402; 530/411
[58] Field of Search .................................. 424/486, 78.17, 424/78.26, 78.3; 514/773, 777, 8; 525/54.2, 54.1; 527/205; 530/395, 402, 356, 410–11, 813

[56] References Cited

U.S. PATENT DOCUMENTS

| | | | |
|---|---|---|---|
| 4,517,295 | 5/1985 | Bracke et al. | |
| 4,931,546 | 6/1990 | Tardy et al. | 530/356 |
| 5,128,326 | 7/1992 | Balazs et al. | 514/54 |

FOREIGN PATENT DOCUMENTS

| | | | |
|---|---|---|---|
| 0 693 523 A2 | 1/1996 | European Pat. Off. | C08H 1/06 |

OTHER PUBLICATIONS

Amiel, et al., 1985, "Rib Perichondrial Grafts for the Repair of Full–Thickness Articular–Cartilage Defects," *J. Bone Joint Surg.* 67A:911–920.

Blein–Sella, O., et al., 1995, "Rabbit Articular Chondrocyte Functional Toxicity Test," *Methods Mol. Biol.* 43:169–75.

Dietz, U., et al., 1993, "Alterations of Collagen mRNA Expression During Retinoic Acid Induced Chondrocyte Modulation: Absence of Untranslated α1(I) mRNA in Hyaline Chondrocytes," *J. Cell Biol.* 52(1):57–68.

Kuettner, K.E., et al. 1992, "Biochemistry of Articular Cartilage in Health and Disease," *Clin. Biochem.* 25:155–63.

Lee, M.K., et al., 1991, "Analysis of affinity and structural selectivity in the binding of proteins to glycosaminoglycans: Development of a sensitive electrophoretic approach," *Proc. Natl. Acad. Sci. USA* 88 (7):2768–72.

Sandell, L.J., et al., 1991, "Alternatively Spliced Type II Procollagen mRNAs Define Distinct Populations of Cells during Vertebral Development: Differential Expression of the AMino–Propeptide," *J. Cell. Biol.* 114 (4):1307–19.

Schmid, T.M., et al., 1985, "Immunohistochemical Localization of Short Chain Cartilage Collagen (Type X) in Avian Tissues," *J. Cell Biol.* 100:598–605.

Spiro, R.C., et al., 1991, "Uncoupling of Chondroitin Sulfate Glycosaminoglycan Synthesis by Brefeldin A," *J. Cell. Biol.*, 115 (5):1463–73.

Thyberg and Moskalewski, 1979, "Bone Formation in Cartilage Produced by Transplanted Epiphyseal Chondrocytes," *Cell Tissue Res.* 204 (1): 77–94.

Wong and Cohn, 1975, "Target cells in bond for parathormone and calcitonin are different: Enrichment for each cell type by sequential digestion of mouse calvaria and selective adhesion to polymeric surfaces," *Proc. Natl. Acad. Sci. USA* 72:3167–71.

*Primary Examiner*—Edward J. Webman
*Attorney, Agent, or Firm*—Fish & Richardson P.C.

[57] ABSTRACT

A matrix and a method for preparing it are provided to support the growth of bone or cartilage tissue. A polysaccharide is reacted with an oxidizing agent to open sugar rings on the polysaccharide to form aldehyde groups. The aldehyde groups are reacted to form covalent linkages to collagen.

20 Claims, No Drawings

COLLAGEN-POLYSACCHARIDE MATRIX FOR BONE AND CARTILAGE REPAIR

BACKGROUND OF THE INVENTION

The invention is directed to a matrix for the therapeutic repair of bone and cartilage tissue, methods of producing such a matrix, and methods of using the matrix to grow bone or cartilage. The use of the matrix is accomplished without utilization of ex vivo cultivation methods.

There is a clinical demand for a bone grafting matrix that offers osteoconductive properties equal to autogenous bone and that can be produced in unlimited supply. Although some bone substitutes are available, many consist of materials that have poor physical handling and resorption characteristics that complicate their use and radiographic evaluation.

Similarly, there is no commercially useful or consistently effective product that supports the maintenance of the chondrocyte phenotype of cartilage tissue, despite years of extensive research. Prior strategies to facilitate the repair of damaged cartilage have included the transplantation of existing host cartilage and/or the implantation of prosthetic devices. Limitations of these methods are the availability of donor tissue and the limited lifespan of prosthetic implants. More recently, the ex vivo cultivation of mature chondrocytes on polymeric scaffolds has been used in an attempt to generate cartilage graft material but this has not yet been widely accepted in part because it involves two surgical procedures: one to harvest chondrocytes and the second to implant them after expansion in vitro.

Collagens and glycosaminoglycans are two classes of biomaterials suited for use in bone regeneration. Collagen-based scaffolds have been used in bone grafting. Type I collagen has good cell adhesive properties, in particular, for bone-forming osteoblast cells. In addition, if desired, the inherent cell adhesion sites can be masked to support increased cell-to-cell interaction and adhesion by the incorporation of non cell-adhesive polymers or polysaccharides. Thus, collagen has the capacity to serve both as an active or inert scaffold material for growth.

Hyaluronic acid is a natural component of the cartilage extracellular matrix, and it is readily sterilized, is biodegradable and can be produced in a wide range of consistencies and formats. It is generally biocompatible and its resorption characteristics can be controlled by the manipulation of monomers to polymer forms, most commonly through the esterification of the carboxylic groups of the glucuronic acid residues.

Dextran sulfate is a glycoaminoglycan-like polyionic derivative of dextran and has been shown to be useful as a biomaterial and drug for treatment of hyperlipidemia. It is produced by esterification of dextran, a hydrophilic polymer of glucose synthesized by certain strains of bacteria.

While these materials have been used separately or in combination with other materials, there has been to date no recognition of combinations and methods of making combinations of such materials to form an advantageous matrix for bone and cartilage repair which does not utilize extraneous cross-linking or ionic binding agents.

SUMMARY OF THE INVENTION

The present invention provides a matrix and methods for preparing a matrix to support the repair of bone and cartilage tissue. The method comprises the steps of oxidizing an exogenous polysaccharide to form a modified exogenous polysaccharide having aldehyde groups, and reacting the modified exogenous polysaccharide with collagen under conditions such that the aldehyde groups covalently react with collagen to form a crosslinked matrix.

The present invention also provides methods of using the matrix to grow bone or cartilage by administering the matrix at the sites of desired repair.

As used in this discussion, repair is defined as growth of new tissue. The basic cellular properties involved in repair include adhesion, proliferation, migration and differentiation.

By conduction, it is meant that the tissue (bone or cartilage) grows by extension on existing tissue cells of the same type.

As used in this discussion, an exogenous polysaccharide refers to a free polysaccharide.

The ratios of the collagen to polysaccharide can be varied to change both the physical and biological properties of the matrix. A higher proportion of collagen will result in a more porous sponge-like matrix. A higher proportion of polysaccharide will result in a more gel-like matrix.

DESCRIPTION OF THE PREFERRED EMBODIMENTS

The method of preparing a matrix of the present invention comprises the steps of opening sugar rings on an exogenous polysaccharide and oxidizing terminal hydroxy groups to aldehydes using, for example, sodium or potassium periodate as a selective oxidizing agent. The amount of aldehyde groups produced in this manner can be stoichiometrically controlled. Typically, from about 1% to 50% of the rings can be opened in this manner. More preferably about 1% to 5% of the rings are opened to form the aldehyde groups. These aldehyde groups can form covalent crosslinks with the collagen at amine sites on the collagen peptide chains. Since the aldehyde groups are formed in situ without the addition of a separate cross-linking compound, the intermolecular distance between the backbone of the polysaccharide chain and the collagen chain which is crosslinked to it is believed to be less than the corresponding distance using a crosslinking compound. Accordingly, the polysaccharide and collagen backbones are relatively closely bound, which produces an advantageous structure for the purpose of providing a matrix that supports or conducts the growth of bone or cartilage tissue.

The starting material for producing the collagen may be purified, native collagen or modified collagen of any type. A preferred collagen for bone growth is Type I collagen, whereas a preferred collagen for cartilage growth is Type II collagen. The collagen may be crosslinked or non-crosslinked, but it is preferred that the collagen be non-crosslinked to provide more accessibility to side groups for crosslinking to the polysaccharide aldehyde groups.

The type of polysaccharides which may be utilized include hyaluronic acid, chondroitin sulfate, dermatan sulfate, keratan sulfate, heparan, heparan sulfate, dextran, dextran sulfate, alginate, and other long chain polysaccharides. Typically, the polysaccharide will have an average molecular weight of about 1,000 to 10,000,000 DA.

The reagents for opening sugar rings on the exogenous polysaccharide may be any selective oxidizing agent which oxidizes a terminal hydroxyl group to an aldehyde, such as potassium or sodium periodate. Other reagents include specific sugar oxidases.

The preferred polysaccharide is hyaluronic acid. The relative proportion of polysaccharide to collagen will impart various physical and biological characteristics to the matrix. The proportion of polysaccharide to collagen may be characterized on a molar ratio basis or on a weight ratio basis. Typically, the ratio by weight of collagen to polysaccharide is from 99:1 to about 1:99. This represents an approximate molar ratio of 99.9:0.1 to 1:9, respectively, assuming an average molecular weight of 1,000,000 daltons for hyaluronic acid and 100,000 daltons for collagen. The molar ratio may vary depending on the actual molecular weight of the polysaccharide and collagen used. In a preferred embodiment disclosed herein, the ratio by weight of collagen to polysaccharide is from 9:1 to about 1:9.

The ratios of the collagen to polysaccharide can be varied to change both the physical and biological properties of the matrix. Biologically, a higher proportion of Type I collagen will more closely mimic the composition and architecture of bone, whereas a higher proportion of Type II collagen will more closely mimic the composition of cartilage. Bone forming cells will interact with specific cell adhesion sites on collagen and will divide, migrate and differentiate to form new bone.

Alternatively, increasing the proportion of polysaccharide, preferably hyaluronic acid, will more closely mimic a natural cartilage matrix. In addition, a higher proportion of polysaccharide will mask some specific cell adhesive sites on collagen and will favor other cell—cell interactions and aggregation important in the development of cartilage tissue.

The matrices according to the present invention may be formed into any shape by lyophilization, or wet-laying and air drying in molds of the desired shape. The lyophilized or wet-layed material having a high proportion polysaccharides may also be formed into viscous gels for injection or direct application into a fracture.

The usefulness of the matrices according to the present invention can be shown by both in vitro and in vivo tests. For the in vitro tests, primary fetal rat calvarial cells, harvested by a series of collagenase digestions, according to the method of Wong and Cohn (*PNAS USA* 72:3167–3171, 1975), or primary rat epiphyseal cartilage Thyberg and Moskalewski, (*Cell Tissue Res.* 204:77–94, 1979) or rabbit articular chondrocytes, harvested by the method of Blein-Sella O. et al., (*Methods Mol. Biol.,* 43:169–175, 1995), are seeded into the matrices and cultured under conventional conditions for 1–4 weeks. Cultures are then processed and evaluated histologically.

The chondroconductive capability of the matrices of the present invention can be determined by successful support of adhesion, migration, proliferation and differentiation of primary rat bone marrow and stromal cells as well as retinoic acid-treated primary rat or rabbit chondrocytes. Bone marrow and bone marrow stromal cells closely approximate the early chondroprogenitor cells found in the subchondral bone marrow of full-thickness defects. Bone marrow are harvested from the long bones of 2–3 week-old inbred Lewis rats and added directly to a matrix and cultured for 2 weeks under standard conditions. The adherent stromal cell population that grows out of these cultures are passaged and frozen for use. Cells from up to six passages are used for culturing or seeding on the matrix.

Retinoic acid-treated chondrocytes represent the latter stages of chondrogenesis. Retinoic acid treatment of primary is performed prior to culturing or seeding the cells on a candidate matrix (Dietz, U. et al., 1993, *J. Cell Biol.* 52(1):57–68).

In an alternative method, in vitro studies of the early and late stage chondrocytes are merged to allow stromal cells to condition the matrices and then to replace them with more mature chondrocytes. In this way, evolution of the matrices during the early phases of chondrogenesis may be tested for effects on the later stages of the process.

Cell adhesion and proliferation on the matrix are monitored using an MTS assay that can measure cell number and viability based on mitochondrial activity. Stromal cells or chondrocytes are cultured on matrices for 6–18 hrs. in the presence or absence of serum for adhesion analysis and for 1–2 weeks for proliferation assessment.

For cell migration testing, matrices are coated or fitted onto porous Trans-well membrane culture inserts (Corning). Stromal cells are seeded on top of the matrices in the upper chamber of the Trans-well and a chemoattractant (growth factor, PDGF) placed in the bottom chamber. After 12–18 hrs of culture the cells that have migrated through the matrix to the bottom side of the Trans-well membrane are quantitated by the MTS assay. Matrices are removed from the upper chamber and processed histologically to assess degree of infiltration.

The analysis of differentiation markers relevant to chondrogenesis and osteogenesis are evaluated at both the protein and transcriptional level. The specific markers that may be analyzed include: 1) Type II collagen and IIA, IIB isoforms; 2) Aggrecan proteoglycan; 3) Type IX, X and XI collagen; 4) Type I collagen; 5) Cartilage matrix protein (CMP); 6) Cart-1 transcription factor; 7) Fibronectin (EDA, EDB isoforms); 8) Decorin proteoglycan; 9) Link protein; 10) NG-2 proteoglycan; 11) Biglycan proteoglycan; 12) Alkaline phosphatase. Differentiation may be measured by Northern/PCR analysis, Western blotting or by metabolic cell labeling.

For Northern/PCR analysis, RNA are isolated by standard procedures from stromal cells or chondrocytes that have been cultured on composite matrices. Time course tests may be used to determine optimal culture periods that range from 1 to 6 weeks depending on the cell type. The isolated RNA is analyzed by Northern gel and hybridization techniques with specific cDNA or PCR amplified probes. Northern analysis is quantified by densitometric scanning of autoradiographs and normalization to housekeeping gene signals (G3PDH). Northern analysis may be supplemented with quantitative PCR analysis using primers generated from the published cDNA sequences of the genes to be analyzed.

For Western blotting, solubilized protein lysates are isolated from cells cultured on composite matrices by standard techniques (Spiro R. C., et al., 1991, *J. Cell. Biol.,* 115:1463–1473). After the lysis of cells the matrices are extracted in stronger denaturants (8M urea, GnHCL) to remove and examine matrix-bound or incorporated proteins. Protein samples are analyzed by standard Western blotting techniques using specific polyclonal or monoclonal antibodies.

For metabolic cell labeling, cells cultured on a composite matrix are metabolically radiolabeled with $^{35}SO_4$, $^{35}S$-methionine or $^3H/^{14}C$-labeled amino acids by standard techniques (Spiro et al., supra). Solubilized cellular and matrix-associated proteins are quantitatively immunoprecipitated with antibodies specific for the protein of interest and analyzed by SDS-PAGE (Spiro et al., supra). Quantitation of results are performed by densitometric scanning of autoradiographs and signals will be normalized to either cell equivalents or to a house-keeping protein such as actin.

Additionally, the ability of a matrix of the present invention to support chondrogeneic differentiation in vivo may be tested in an inbred rat soft tissue implant model. Rat bone marrow or stromal cells described above are seeded onto matrices at high density, cultured overnight in αMEM medium containing 10% FBS serum and antibiotics, then transferred into Millipore diffusion chambers and implanted intraperitoneally or subcutaneously into 8 week-old recipients. Chambers are harvested after 3 weeks and evaluated histologically for cartilage formation.

A transplantation model in outbred rats is used to evaluate the ability of the composite matrices to maintain the cartilage phenotype in vivo. Rib costal cartilage chondrocytes are seeded onto matrices at high density and cultured overnight in Ham's F-12 containing 1% rat serum and antibiotics. The seeded matrices are then implanted into posterior tibial muscle pouches created by blunt dissection in 8 week-old male Sprague-Dawley rats. Explants are taken at 14 and 28 days and evaluated histologically for matrix compatibility, cartilage growth, and maintenance of the differentiated phenotype based on staining for aggrecan and type II collagen.

In addition, the ability of a matrix of the present invention to interact with extracellular matrix proteins (proteoglycans, proteins and growth factors) found in the surrounding serum, tissue fluid, or in the secretion products of chondroprogenitor cells correlate with the chondroconductive potential of a matrix. The interaction of the matrices of the present invention with extracellular matrix proteins may be measured by means known to those of skill in the art such as, Western blotting, affinity co-electrophoresis techniques and binding characteristics.

To assay serum protein binding to a matrix of the present invention, the matrix is incubated in culture media containing increasing amounts of serum (various species and sources). After washing, bound proteins are eluted by boiling in SDS-PAGE sample buffer and unsolubilized matrix will be removed by centrifugation. SDS-PAGE analysis is used to initially document the binding pattern of the matrices. Western blotting is then performed to identify specifically bound components such as fibronectin and vitronectin.

Affinity coelectrophoresis is used to analyze proteoglycan binding to a matrix of the present invention. $^{35}SO_4$-labeled or iodinated proteoglycan (aggrecan) isolated from bovine and rat (or other sources) is loaded into ACE gels (Lee, M. K. et al., 1991, 88:2768–2772) containing composite matrices or collagen scaffolds alone. The binding affinity of aggrecan for collagen scaffolds plus and minus hyaluronic acid or dextran sulfate are taken as a measure of the ability of composite matrices to organize a cartilage matrix.

An evaluation of protein interactions with collagen-based composite matrices can potentially be hindered by the large excess of collagen protein. The collagen scaffolds have enough inherent structural integrity and are crosslinked to an extent that will prevent their complete solubilization, but some collagen protein may become solubilized in the SDS-PAGE sample buffer. Thus, this could obscure the visualization of other bound proteins, particularly the cell-synthesized collagens, and may also cause high background in Western blot analysis. Therefore, an alternative approach is to use radiolabeled or biotinylated proteins for the binding analysis. Serum proteins may be biotinylated prior to incubation with the composite matrices and then developed with avidin-based reagents. Both approaches allow the visualization of matrix-associated components without the interference of the scaffold collagen protein.

Alternatively, the shift in expression from Type I to Type II collagen and the splicing of the Type II collagen transcript from the Type IIA to the Type IIB isoform (Sandell, L. J. et al., 1991, *J. Cell Biol.* 114:1307–1319) are measured by means known to those of skill in the art to determine differentiation down a chondrogenic pathway. Also, the expression of the cartilage-associated proteoglycan, aggrecan (Schmid, T. M., et al., 1985, *J. Cell Biol.* 100:598–605 and Kuettner K. E. 1992, *Clin. Biochem.* 25:155–163) and a cartilage homeoprotein transcription factor (Cart-1) appear to be markers for cells committed to the chrondrocytic lineage.

For the in vivo tests, the matrices are evaluated for the capabilities for supporting osseous healing in a rat cranial defect model by implantation into a 5 mm by 3 mm defect created in the parietal bone of 6 weeks old male Sprague-Dawley rats. The defects are evaluated at 28 days by radiographic and histologic analysis.

The in vivo model for cartilage repair is a full-thickness articular cartilage defect in the rabbit (Amiel et al., 1985, *J. Bone Joint Surq.* 67A:911). Defects measuring approximately 3.7 mm in diameter and 5 mm deep defect are created in the center of the medial femoral condyles of adult male New Zealand white rabbits. The defects are then either filled with matrix or left unfilled as controls. The defects are evaluated morphologically and histologically at 6 and 12 weeks.

The matrices of the present invention may be used for the treatment of bone and/or cartilage defects associated with surgical resection, such as spinal fusions; trauma; disease; infection; cancer or genetic defects. The matrices according to the present invention may be administered through implantation, direct application or injection depending on the intended application of the matrix, the physical properties of the matrix and the ratio by weight of collagen to polysaccharide in the matrix.

In one aspect of the present invention, the matrix has a higher proportion of collagen compared to polysaccharide, is in a sponge-like form and is surgically implanted at a site where growth of new bone tissue is desired, such as in spinal fusions. Alteratively, in another aspect of the present invention, the matrix has a higher proportion of polysaccharide compared to collagen, is formed into a viscous gel and is either directly applied or injected into a site where growth of new bone tissue is desired, such as in filling bone defects, fracture repair and grafting periodontal defects. In yet another aspect of the present invention, the matrix has a higher proportion of polysaccharide, is formed into a viscous gel and is injected directly or delivered through an arthoscopic procedure into a site where growth of cartilage tissue is desired, such as in injury induced cartilage damage or disease-induced cartilage damage such as in, osteoarthritis or rheumatoid arthritis. As will be understood by those of skill in the art, the amount of matrix to be administered to conduct growth of bone or cartilage tissue depends upon the extent of the bone or cartilage defect to be treated.

The following examples are provided for purposes of illustration and are not intended to limit the invention in any way.

EXAMPLE 1

This example illustrates the production of a variety of matrices for use in bone and/or cartilage repair. In the following matrices, Type I collagen was used as a raw material. Semed F collagen (Type I, insoluble) and Semed S collagen (Type I, acid soluble) were from Kensey-Nash. Hyaluronic-polyaldehyde, dextran-polyaldehyde, dextran sulfate/polyaldehyde, and chondroitin sulfate/polyaldehyde were prepared by oxidation of the related polysaccharide with reagent grade sodium periodate.

The matrix in this case was based on the reaction of protein amine residues on the collagen with the active aldehyde groups generated on the sugar rings of the polysaccharides. Matrices with various surface properties and biological activity are synthesized by controlling the ratios of the collagen to the polysaccharides, the type of collagen, the types of polysaccharides, as well as the density of the aldehyde groups generated on the polysaccharides.

Semed F collagen (8.1 parts) and Semed S collagen (0.9 part) were dispersed in a hyaluronate/polyaldehyde solution (1 part, 5% of the repeat units were oxidized: pH 3–3.5) containing 10 mM sodium cyanoborohydride ($NaCNBH_3$) in a heavy duty blender at low speed for 10 seconds followed by high speed for another 5 seconds. The slurry (solids concentration: 28 mg/ml) was poured into a mold, incubated at ambient temperature for 24 hours and lyophilized. This formed a sponge which was washed several times in distilled water to completely remove the $NaCNBH_3$. The washed sponge was then lyophilized.

The above procedure was followed to make other matrices using the starting materials as follows:

| | |
|---|---|
| Semed F collagen (0.9 part) Semed S collagen (0.1 part) | Hyaluronate/polyaldehyde solution (1 part, 5% of the repeat units oxidized) Solids concentration: 15 mg/ml |
| Semed F collagen (0.9 part) Semed S collagen (0.1 part) | Hyaluronate/polyaldehyde solution (2 parts, 5% of the repeat units oxidized) Solids concentration: 15 mg/ml |
| Semed F collagen (0.9 part) Semed S collagen (0.1 part) | Hyaluronate/polyaldehyde solution (4 parts, 5% of the repeat units oxidized) Solids concentration: 15 mg/ml |
| Semed F collagen (0.9 part) Semed S collagen (0.1 part) | Hyaluronate/polyaldehyde solution (4 parts, 1% of the repeat units oxidized) Solids concentration: 15 mg/ml |
| Collagen Type II (9 parts) | Hyaluronate/polyaldehyde solution (1 part, 5% of the repeat units oxidized) Solids concentration: 15 mg/ml |
| Collagen Type II (1 part) | Hyaluronate/polyaldehyde solution (1 part, 5% of the repeat units oxidized) Solids concentration: 15 mg/ml |
| Semed F collagen (7 parts) Collagen Type II (2 parts) | Hyaluronate/polyaldehyde solution (1 part, 5% of the repeat units oxidized) Solids concentration: 15 mg/ml |
| Semed F collagen (8.1 parts) Semed S collagen (0.9 part) | Dextran/polyaldehyde solution (1 part, 5% of the repeat units oxidized) Solids concentration: 28 mg/ml |
| Semed F collagen (8.1 parts) Semed S collagen (0.9 part) | Dextran sulfate/polyaldehyde (1 part, 5% of the repeat units oxidized) Solids concentration: 28 mg/ml |
| Semed F collagen (8.1 parts) Semed S collagen (0.9 part) | Chondroitin sulfate/polyaldehyde (1 part, 5% of the repeat units oxidized) Solids concentration: 28 mg/ml |
| Semed F collagen (0.9 part) Semed S collagen (0.1 part) | Hyaluronate/polyaldehyde solution (4 parts, 5% of the repeat units oxidized) Solids concentration: 15 mg/ml |

EXAMPLE 2

The matrices of Example 1 were evaluated for their capability of supporting osseous healing in a rat cranial defect model. A matrix of the present invention comprising 1 part collagen (Semed F collagen 0.9 part: Semed 0.1 part) to 1 part hyaluronate/polyaldehyde solution (5% of the repeat units oxidized from solids concentration at 15 mg/ml) was implanted into a 5 mm by 3 mm defect created in the parietal bone of 6 weeks odd male Sprague-Dawley rats. The defects were evaluated at 28 days by radiographic and histologic analysis. The radiographic analysis of the defects suggests that significant bony healing had occurred to unfilled defects. All matrix-filled defects were completely radiodense, with no distinctive defect borders, which indicated complete healing. Unfilled defects appeased as ovoid radiolucent areas with rounded corners, suggesting minimal healing.

The histologic evaluation correlated with radiographic results. The defects were filled with a continuous patch of woven bone that was normal in cellularity and structure, with presumptive marrow spaces and maturing hemopoietic marrow. Traces of residual implant material were shown along with a mild chronic inflammatory infiltrate. In some areas, the new bone was deposited within the interstices of the implant material and bone surfaces were lined with active osteoblasts. These results demonstrate that the implantation of a collagen polysaccharide-polyaldehyde matrix conducted the bone formation of normal repairable bone in this critical defect model.

EXAMPLE 3

This example illustrates that a matrix of the present invention will support the maintenance of chondrocyte phenotype in vitro.

Primary rat chondrocytes made by the method of Blein-Sella O. et al., supra, were seeded into a matrix made by the method disclosed in Example 1 comprising 1 part collagen (Semed F collagen 0.9 part: Semed 0.1 part) to 1 part hyaluronate/polyaldehyde solution (5% of the repeat units oxidized from solids concentration at 15 mg/ml) and cultured under conventional conditions for 1–4 weeks. Cultures were then processed and evaluated histologically. The results show that calvarial cells seed on the matrix grow and continue to express alkaline phosphatase, a marker for bone-forming cells. Chondrocytes seeded on the matrix also proliferate and synthesize a metachromatic staining extracellular matrix indicative of a high proteoglycan content that is typical of the chondrocyte phenotype.

EXAMPLE 4

Matrices made by the process described in Example 1 comprising various ratios of collagen to polysaccharide are implanted into a full-thickness articular cartilage defect in the rabbit as described in Amiel et al., supra. Defects measuring approximately 3.7 mm in diameter and 5 mm deep defect are created in the center of the medial femoral condyles of adult male New Zealand white rabbits. The defects are then either filled with matrix or left unfilled as controls. The defects are evaluated morphologically and histologically at 6 and 12 weeks.

What is claimed is:

1. A method for preparing a matrix to support the repair of cartilage or of bone comprising the steps of oxidizing an exogenous polysaccharide to form a modified exogenous polysaccharide having aldehyde groups, and reacting said modified exogenous polysaccharide with collagen under conditions whereby said aldehyde groups covalently react to crosslink with collagen to form said matrix.

2. A method according to claim 1, wherein said polysaccharide comprises hyaluronic acid, chondroitin sulfate, dermatan sulfate, keratan sulfate, heparan, heparan sulfate, dextran, dextran sulfate, or alginate.

3. A method according to claim 2, wherein said polysaccharide is hyaluronic acid.

4. A method according to claim 1, wherein said steps of oxidizing said polysaccharide comprises treatment of said polysaccharide with periodate.

5. A method according to claim 1, wherein said collagen and said polysaccharide used to form said matrix are present in the range of 99:1 to 1:99 by weight, respectively.

6. A method according to claim 1, wherein about 1% to 50% of the repeat units in said polysaccharide are oxidized to contain aldehyde groups.

7. A method according to claim 6, wherein about 1% to 5% of the repeat units in said polysaccharide are oxidized to contain aldehyde groups.

8. A method according to claim 1, wherein said matrix is formed by freezing and lyophilization.

9. A method according to claim 1, wherein said matrix is formed by wet laying and air drying.

10. A matrix to support the repair of cartilage or bone, said matrix comprising collagen covalently crosslinked to an exogenous polysaccharide, wherein said polysaccharide is crosslinked to said collagen through oxidized sugar rings on said polysaccharide which form covalent linkages to said collagen.

11. A matrix according to claim 9 wherein said polysaccharide comprises hyaluronic acid, chondroitin sulfate, dermatan sulfate, keratan sulfate, heparan, heparan sulfate, dextran, dextran sulfate or alginate.

12. A matrix according to claim 11 wherein said polysaccharide is hyaluronic acid.

13. A matrix according to claim 10 wherein said matrix comprises said collagen and said polysaccharide in a weight ratio in the range of 99:1 to 1:99.

14. A method of conducting the growth of bone tissue in vivo comprising the step of administering a matrix according to claim 10 at a site of desired bone growth.

15. A method of conducting the growth of cartilage tissue in vivo comprising the step of administering a matrix according to claim 10 at a site of desired cartilage growth.

16. A method according to claim 14 wherein said polysaccharide comprises hyaluronic acid, chondroitin sulfate, dermatan sulfate, keratin sulfate, heparan, heparan sulfate, dextran, dextran sulfate or alginate.

17. A method according to claim 15 wherein said polysaccharide comprises hyaluronic acid, chondroitin sulfate, dermatan sulfate, keratin sulfate, heparan, heparan sulfate, dextran, dextran sulfate or alginate.

18. A method according to claim 16 wherein said polysaccharide is hyaluronic acid.

19. A method according to claim 17 wherein said polysaccharide is hyaluronic acid.

20. A method according to claim 1 wherein said step of reacting said modified exogenous polysaccharide with collagen comprises reacting said polysaccharide and collagen in the presence of sodium cyanoborohydride.

* * * * *